United States Patent [19]

Neal et al.

[11] 4,075,489
[45] Feb. 21, 1978

[54] METHOD AND APPARATUS INVOLVING THE GENERATION OF X-RAYS

[75] Inventors: William R. Neal; Roger G. Little, both of Bedford, Mass.

[73] Assignee: Simulation Physics, Bedford, Mass.

[21] Appl. No.: 761,064

[22] Filed: Jan. 21, 1977

[51] Int. Cl.$^2$ .............................................. H05G 1/30
[52] U.S. Cl. .................................. 250/401; 250/402; 250/403; 250/445 T; 313/330
[58] Field of Search ............... 250/401, 402, 403, 404, 250/405, 445 T; 313/55, 330

[56] References Cited

U.S. PATENT DOCUMENTS

| 2,946,892 | 7/1960 | Bas-Taymay | 250/404 |
| 3,106,640 | 10/1963 | Oldendorf | 250/445 T |

*Primary Examiner*—Craig E. Church
*Attorney, Agent, or Firm*—Morse, Altman, Oates & Bello

[57] ABSTRACT

An electron gun assembly generates an accelerated and sharply focused electron beam which is deflected in a predetermined path to impinge upon an extended split anode structure in a selected scanning pattern with approximately half the beam current impinging on each half of the split anode. A signal proportional to the difference between the two currents from each half of the split anode provides feedback control to the beam deflection system for constraining the beam to follow the fissure of the split anode. X-rays which are generated at the point of beam impingement on the split anode constitute a moving source of X-rays as the point of beam impingement travels in the selected pattern along the anode.

15 Claims, 2 Drawing Figures

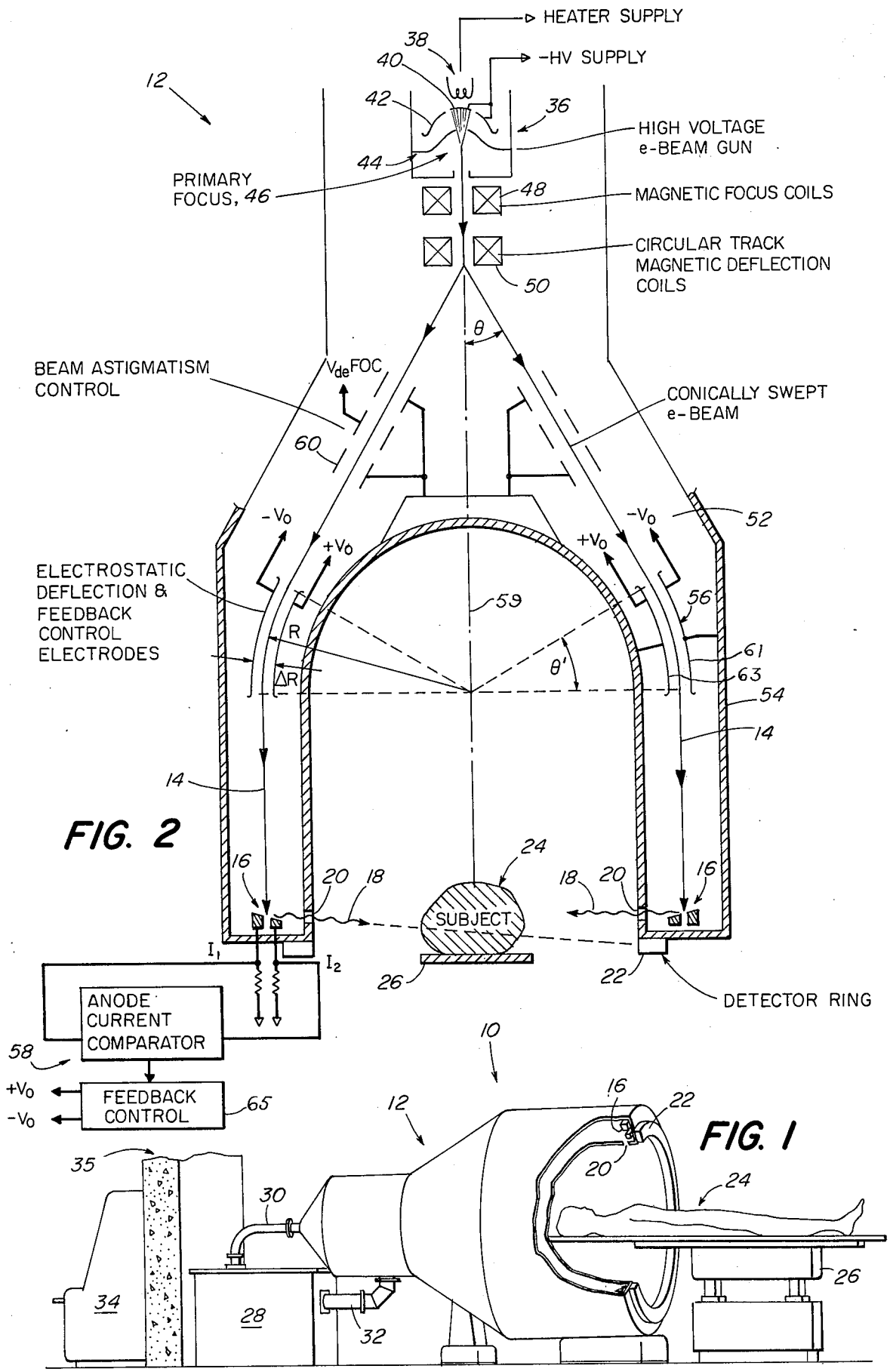

METHOD AND APPARATUS INVOLVING THE GENERATION OF X-RAYS

BACKGROUND OF THE INVENTION

1. Field of the Invention

The present invention relates to X-rays and, more particularly, is directed towards a method and apparatus for the generation of X-rays.

2. Description of the Prior Art

X-ray tomography for medical diagnostic processes involves the use of a moving source of X-rays for producing either a single cross-sectional density profile of an irradiated subject under diagnosis or a three dimensional density profile from a spatially separated sequence of such cross-sectional profiles. Since it is necessary to irradiate the subject from a large number of different directions in a common cross-sectional plane, the X-ray source encircles or scans the subject for at least one half an orbit and, in many instances, for an entire orbit.

Prior art approaches for moving the X-ray source involve the direct mechnical transport of a standard vacuum X-ray generating tube and its associated high voltage cables. In order to eliminate blurring of the density profile due to subject motion such as respiration and heart beat, it is necessary that the total scan time is made to be substantially less than the time intervals characteristic of such subject motions. Due to the difficulties associated with faster mechanical transport of the X-ray tube, and such associated problems as coiling and uncoiling high voltage cables, attempts at increased scan rates have been met with qualified acceptance. Systems of the type shown in U.S. Pat. No. 3,106,640 for providing a moving source of X-rays by deflecting a rotating beam onto a circular target have been introducted with varying degrees of success.

The need for increased X-rays intensity for maintaining density profile quality has resulted in increased heat production within the X-ray tube. Dissipation of this increase heating, by water cooling for example, becomes impractical with conventional X-ray tubes due to the intended high transport velocity. The use of a rapidly spinning anode, in conjunction with selected beam-on heating time intervals and beam-off cooling time intervals, for heat control and dissipation, which is the present technological state of the art for conventional X-ray tubes, has been met with a limited degree of success.

SUMMARY OF THE INVENTION

An object of the present invention is to provide a method and apparatus for generation of X-rays which does not suffer from the limitations heretofore discussed.

Another object of the present invention is to provide a method and apparatus for generation of X-rays from a moving source without the mechanical transport limitations of the prior art teachings.

A further object of the present invention is to provide a method and apparatus for generation of X-rays from a moving source by feedback controlled electron beam deflection. According to the invention, an accelerated and sharply focused electron beam generated by an electron gun assembly is deflected in a predetermined pattern and is directed towards a fixed, extended split anode structure. The electron beam impinges upon the anode structure in a preselected scanning pattern with approximately half the beam current impinging on each half of the split anode. A signal proportional to the difference between the two currents from the split anode segments (e.g. as derived from a differential amplifier) is used for feedback control of the electron beam deflection system, thereby constraining the electron beam to follow precisely the fissure of the split anode structure. Each point of electron beam impingement on the anode structure constitutes a source for generation of X-rays, a continuous series of such sources provided as the electron beam scans the anode structure. The X-rays generated by the series of sources continuously disposed about the anode are directed through collimator openings towards a discrete series of detectors. A subject under diagnosis is positioned between the anode structure and detectors. The X-rays generated from the sources at the points of electron beam impingement upon the anode and directed towards the subject under diagnosis are sensed by the detectors for providing a cross-sectional density profile of the irradiated subject or a separated sequence thereof.

Other objects of the present invention will in part be obvious and will in part appear hereinafter.

The invention accordingly comprises the methods, apparatuses and systems, together with their parts, steps, elements and interrelationships that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein:

FIG. 1 is a perspective view, partly in section, of a tomographic system having an X-ray source embodying the invention; and FIG. 2 is a block and schematic diagram of the X-ray source of FIG. 1.

DETAILED DESCRIPTION OF THE PREFERRED EMBODIMENTS

Referring now to the drawings, particularly FIG. 1, there is shown a tomographic X-ray system 10 embodying the invention. System 10 comprises an X-ray source 12 for generating an accelerated and sharply focused electron beam 14 which is deflected in a predetermined path for impingement upon a stationary split anode structure 16 in a selected scanning pattern. Each point of electron beam 14 impingement upon split anode structure 16 constitutes a source of X-rays, a series of such sources being momentarily established as the electron beam travels in the controlled scanning pattern along the fissure of the split anode structure. X-rays 18, which are generated at the points of impingement of the electron beam on anode structure 16, are directed through collimator openings 20 towards a ring of detectors 22. A subject 24 under diagnosis is positioned between anode structure 16 and detectors 22.

Subject 24 is lying on a multi-positionable platform 26 which is adjusted so that the subject is positioned centrally of anode structure 16, the particular portions of the subject under diagnosis being disposed between the split anode structure and detectors 22 in the travel path of X-rays 18. X-ray source 12 is interconnected with a voltage and vacuum supply 28 by means of suitable electrical cables 39 and vacuum lines 32. Supply 28 is connected to a controller 34, for example an operator's console. A shield 35 disposed between operators' console 34 and X-ray source 12 protects an operator against the effects of X-rays generated by source 12.

As best shown in FIG. 2, X-ray source 12 includes an electron gun assembly 36 having a heater 38, a cathode 40, a control electrode 42, and an accelerating electrode 44. Electron gun assembly 36 generates an accelerated and sharply focused electron beam which is directed towards a primary focus 46 and is refocused at the anode structure 16 by focus coil 48. The focused beam is deflected in a predetermined path by a deflection systems 50 and 56 for scanning of split anode structure 16 in a selected pattern. In the illustrated embodiment, split anode structure 16 is in the form of a split annulus having a substantially triangular profile in right cross section. Electron gun assembly 36 and split anode 16 are located within an enclosure 52 that is evacuated to a pressure consistent with efficient electron beam propogation. A shield 54, for example a lead shield, surrounds portions of enclosure 52 about the beam flight path and anode structure 16.

As previously indicated, the accelerated and shaprly focused electron beam is deflected in a predetermined path by deflection system 50 and 56. Deflection system 50 deflects the electron beam into a conical pattern at a cone angle $\theta$ about a symmetrical axis 59 towards deflection system 56, for example a pair of electrodes 61 and 63. The distance from symmetrical axis 59 to the midpath of electrodes 61 and 63 is denoted R and the spacing between the electrodes is $\Delta R$. The curvature of electrodes 59 and 61 is such that the electron beam is deflected at an angle $\theta'$ which is equal to the cone angle $\theta$. That is, deflection system 56 is operative to deflect the electron beam into a path that is parallel to symmetrical axis 59. In consequence, the electron beam impinges upon split anode structure 16 in a selected scanning pattern with approximately half the beam current impinging on each half of the split anode. A signal proportional to the difference between the two currents $I_1$ and $I_2$ from the split anode segments is generated by an anode current comparator 58, for example a differential amplifier. The proportional signal is applied to a controller 65 which generates different signals $+V_o$ and $-V_o$ for feedback control of deflection system 56. The different signals constitute feedback signals for controlling deflection system 56 so that the electron beam is constrained to follow the fissure of split anode structure 16. Anode structure 16 is composed of a material that is characterized by emission of X-rays when struck by the electron beam. Preferably, anode structure is composed of a high atomic number element. Tungsten, having a high atomic number as well as being refractory, is the commonly employed element. In the illustrated embodiment which includes an anode structure in the form of a split ring, the locus of the predetermined deflection path of the electron beam discribes a conical scanning pattern. In the illustrated embodiment deflection system 50 is a magnetic deflection system. In an alternate embodiment, deflection system 50 is an electrostatic deflection system.

As the electron beam is deflected into a conical scanning pattern, the beam impinges upon split annular anode structure 16. Impingement of the accelerated and sharply focused beam upon anode 16 results in generation of X-rays at the point of impingement. As the point of beam impingement travels about anode structure 16, a series of X-ray generating sources is established. The temperature at a given point in annular anode 16 rises rapidly during the brief interval in which the electron beam traverses the point and then relaxes back towards the pre-beam-pass value by thermal radiation and conduction into the bulk mass of the anode until the next beam passage.

For a given intensity of electron beam 14, the rapid temperature rise in anode structure 16 can be reduced substantially if the area of impingement of electron beam 14 is elongated in the direction of the subject 24. To produce this elongation, whose direction must continuously rotate with the conical deflection of electron beam 14, a controlled astigmatism is introduced by means of a controller 60, for example, a cylindrical Einzel Lens 60.

In the preferred embodiment, the range of X-ray system 10 characteristics are as follows:

| | |
|---|---|
| Electron Energy | 100–150 keV |
| Electron Current | 50–500 milliamperes |
| Spot Diameter | 2.0–4.0 millimeters |
| Scan Time | 0.1–100 seconds |
| Intensity | $10^{10}-10^{11}$ photons/sec/cm$^2$ at detector location |

It will be apparent from the foregoing discussion that the present invention provides a method and apparatus for sequentially generating X-rays from a plurality of sources momentarily established at the points of impingement of an accelerated and sharply focused electron beam upon a split anode structure. Movement of the beam about the anode is provided by magnetically or electrostatically deflecting the beam in a predetermined path corresponding to the fissure profile of the split anode structure. In the illustrated embodiment, the profile of the anode describes a split ring and a predetermined path is then conical. The spot diameter of the beam impinging upon the anode structure is 2–4 millimeters. The X-rays generated by the sources are directed through collimator openings towards a series of X-ray detecting devices, a subject under diagnosis being positioned between the sources and detectors in the travel path of the X-rays. The detected X-rays, which have passed through the subject, provide the information necessary to construct a cross-sectional density profile of the particular portions of the subject of interest, a three dimensional density profile obtained from a spatially separated sequence of such cross-sectional profiles. The invention thus provides a plurality of X-ray sources from a single electron gun assembly and a single anode structure, the sources being momentarily established as the electron beam impinges upon the anode in a predetermined pattern controlled by selected deflection of the beam.

Since certain changes may be made in the foregoing disclosure without departing from the scope of the invention herein involved, it is intended that all matter contained in the above description and depicted in the accompanying drawing be construed in an illustrative and not in a limiting sense.

What is claimed is:

1. A method for producing a plurality of distributed X-ray generating sources comprising the steps of:
   (a) generating an electron beam having sufficient electron energy for causing emission of X-rays;
   (b) directing said electron beam towards a split anode structure composed of a material that emits X-rays upon impingement of said electron beam;

(c) scanning said split anode structure in a selected pattern with said electron beam, whereby X-rays are generated at the points of electron beam impingement upon said split anode structure, each point of beam impingement constituting an X-ray generating source.

2. The method as claimed in claim 1 wherein said directing step includes deflecting said electron beam in a predetermined path for impingement upon said split anode structure in a selected pattern and generating a signal for controlling said deflection, said signal being a feedback signal derived from the partitioning of said electron beam between two segments of said split anode, thereby constraining said electron beam to follow precisely the fissure between said segments of said split anode.

3. The method as claimed in claim 1 wherein said electron beam generating step includes accelerating and focusing said electron beam.

4. The method as claimed in claim 3 wherein said electron beam has an electron energy in the range of 100 to 150 keV and a scan rate in the range of 0.1 to 100 seconds.

5. A method for producing a plurality of distributed X-rays generating sources comprising the steps of:
   (a) generating an accelerated and focused electron beam having sufficient electron energy for causing emmision of X-rays;
   (b) directing said electron beam towards a split anode structure composed of a material that emits X-rays upon impingement of said electron beam; and
   (c) deflecting said electron beam for impingement upon said split anode structure in a selected pattern and generating feedback signals derived from beam currents at segments of said split anode structure for constraining said electron beam to follow the fissure of said split anode structure, whereby X-rays are generated at points of electron beam impingement upon said split anode structure, said points of beam impingement constituting a plurality of X-rays generating sources that are distributed about said split anode structure along the travel path of said electron beam.

6. The method as claimed in claim 5 wherein said deflecting step includes magnetically deflecting said electron beam.

7. The method as claimed in claim 5 wherein said deflecting step includes electrostatically deflecting said electron beam.

8. A system for producing a plurality of distributed X-ray sources, said system comprising:
   (a) a split anode structure composed of a material which emits X-rays upon impingement by an electron beam;
   (b) an electron gun assembly for generating an electron beam having sufficient electron energy for causing emission of X-rays from said split anode structure; and
   (c) means for moving said electron beam in a predetermined path for impingement upon said split anode structure in a selected pattern, said electron beam constrained to follow the fissure of said split anode structure;
   (d) X-rays generated at the points of impingement of said electron beam and said anode structure, each point of beam impingment constituting a source for generating of X-rays, said sources distributed about said anode structure along the travel path of said electron beam.

9. The system as claimed in claim 8 wherein said means for moving is magnetic deflection means.

10. The system as claimed in claim 8 wherein said means for moving is electrostatic deflection means.

11. A tomographic X-rays system comprising:
    (a) split anode means composed of a material which emits X-rays upon impingement by an electron beam;
    (b) means for generating an electron beam having sufficient electron energy for causing emission of X-rays from said anode means;
    (c) an enclosure within which said anode means and electron beam generating means are disposed;
    (d) means for moving said electron beam in a predetermined path for impingement upon said anode means in a selected pattern and for constraining said electron beam to folow the fissure of said split anode means;
    (e) detector means spaced from said anode means;
    (f) X-rays generated at the points of impingement of said electron beam and said anode means directed towards said detector means, each point of beam impingement constituting a source for generation of X-rays, said sources distributed about said anode means along the travel path of said electron beam.

12. The tomographic X-ray system as claimed in claim 11 wherein said moving means is beam deflecting means.

13. The tomographic X-ray system as claimed in claim 12 wherein said beam deflecting means is electrostatic beam deflecting means, said electron beam moved in a conical scan pattern.

14. The tomographic X-ray system as claimed in claim 11 wherein said electron beam has an electron energy in the range of 100 to 150 keV, an electron current in the range of 50 to 500 milliamperes and a spot diameter at the point of impingement in the range of 2.0 to 4.0 millimeters.

15. The tomographic X-ray system as claimed in claim 14 wherein the scan rate of said electron beam is in the range of 0.1 to 100 seconds and the intensity of said X-rays at said detector means is in the range of $10^{10}$ to $10^{11}$ photons/sec/cm$^2$.

* * * * *